US008500980B1

(12) United States Patent
Amirkhanian et al.

(10) Patent No.: US 8,500,980 B1
(45) Date of Patent: *Aug. 6, 2013

(54) METHOD AND APPARATUS FOR HIGH SPEED GENOTYPING

(75) Inventors: Varouj Amirkhanian, La Crescenta, CA (US); Ming-Sun Liu, Brea, CA (US)

(73) Assignee: Qiagen Sciences, LLC, Germantown, MD (US)

( * ) Notice: Subject to any disclaimer, the term of this patent is extended or adjusted under 35 U.S.C. 154(b) by 217 days.

This patent is subject to a terminal disclaimer.

(21) Appl. No.: 11/977,726

(22) Filed: Oct. 24, 2007

Related U.S. Application Data

(60) Provisional application No. 60/854,218, filed on Oct. 24, 2006.

(51) Int. Cl.
*G01N 27/447* (2006.01)
*G01N 27/453* (2006.01)

(52) U.S. Cl.
USPC ............... 204/455; 204/605; 205/780.5

(58) Field of Classification Search
USPC ............ 204/451, 455, 456, 605; 205/780.5
See application file for complete search history.

(56) References Cited

U.S. PATENT DOCUMENTS

| | | | | |
|---|---|---|---|---|
| 5,164,055 | A * | 11/1992 | Dubrow | 204/455 |
| 5,213,669 | A * | 5/1993 | Guttman | 204/452 |
| 6,828,567 | B2 * | 12/2004 | Amirkhanian et al. | 250/458.1 |
| 7,208,072 | B2 * | 4/2007 | Amirkhanian et al. | 204/603 |
| 7,309,409 | B2 * | 12/2007 | Amirkhanian et al. | 204/603 |
| 2005/0016852 | A1 * | 1/2005 | Amirkhanian et al. | 204/600 |
| 2005/0189219 | A1 * | 9/2005 | Amirkhanian et al. | 204/403.01 |

OTHER PUBLICATIONS

Copending U.S. Appl. No. 11/983,814, "Method and Appartus for High Speed Carbohydrate Analysis".*
Guttman et al., "Capillary Electrophoresis Separation of Oligosaccharides: I. Effect of Operational Variables," Electrophoresis 1994, 15, pp. 1518-1522.
Guttman et al., "Capillary Gel Electrophoresis Separation of High-Mannose Type Oligosaccharides Derivatized by 1-Aminopyrene-3,6,8-Trisulfonic Acid," Electrophoresis 1995, 16, pp. 1906-1911.

* cited by examiner

*Primary Examiner* — Keith Hendricks
*Assistant Examiner* — Susan D Leong
(74) *Attorney, Agent, or Firm* — Liu & Liu (57) ABSTRACT

A cost-effective multi-channel capillary gel-electrophoresis system for highly efficient, nucleic acid-based analysis, in particular HLA SSP (Human Leukocyte Antigen Sequence Specific Primer) typing applications. Twelve DNA samples are automatically injected, electrophoretically separated, detected and analyzed simultaneously by using a multiple usage and disposable multi-capillary gel-cartridge. Using commercially available DNA size markers as indicators, the system provides high resolving power with 12-channel separations in less than 1.5 minutes. The system can hold a total of 96 samples in a PCR plate that can automatically be analyzed within 25 minutes for a full plate of the HLA SSP kits.

24 Claims, 11 Drawing Sheets

Method Name:

| DM80.mtd | | | | | | | |
|---|---|---|---|---|---|---|---|
| Action | | Value | | Duration | | Position | |
| Purge | ▼ | 0.0 | ▼ | 5.0 | ▼ | WP | ▼ |
| Inject | ▼ | 15.0 | ▼ | 8.0 | ▼ | MARKER1 | ▼ |
| Inject | ▼ | 0.0 | ▼ | 0.0 | ▼ | WI | ▼ |
| Sample Injec | ▼ | 15.0 | ▼ | 8.0 | ▼ | A | ▼ |
| Separate | ▼ | 15.0 | ▼ | 80.0 | ▼ | BUF | ▼ |
| Purge | ▼ | 0.0 | ▼ | 0.0 | ▼ | WP | ▼ |
| | ▼ | | ▼ | | ▼ | | ▼ |
| | ▼ | | ▼ | | ▼ | | ▼ |
| | ▼ | | ▼ | | ▼ | | ▼ |
| | ▼ | | ▼ | | ▼ | | ▼ |

FIG. 11

METHOD AND APPARATUS FOR HIGH SPEED GENOTYPING

This application claims the priority of U.S. Provisional Patent Application No. 60/854,218, filed on Oct. 24, 2006. This Provisional Patent Application is fully incorporated by reference herein, as if fully set forth herein. All other applications, patents, documents and references identified in the disclosure herein below, are fully incorporated by reference as if fully set forth herein.

BACKGROUND OF THE INVENTION

1. Field of the Invention

The present invention relates to bio-analysis system and method, and particularly an improved system and method for genotyping.

2. Description of Related Art

The achievement of the Human Genome Project (HGP) was entirely performed by fluorescence Sanger dideoxyribonucleotide sequencing. Since the completion of the Human Genome Project, more than 30,000 genes that are involved in the function of the body have been found in a single human cell. The information from genetic (DNA) analysis has the potential to revolutionize the diagnosis, prevention and treatment of human diseases. Genetic analysis currently is used for identifying drug resistant strains, infectious disease testing applications in bioterrorism, disease diagnostics and prognostics (cancer, cardiovascular disease, Alzheimer's disease), diagnosis of inherited disorders, molecular tissue pathology, forensic identity/testing and pharmacogenetics (therapy selection, monitoring, adverse). Molecular diagnostics (MDx) is the fastest growing segment in the in vitro diagnostics (IVD) market with global market of approximately $2.5 billion, increasing at 15% CAGR in 2005, up from essentially nothing five years ago. Molecular diagnostics is the detection of DNA variation or RNA expression with the intent to diagnose disease, or to determine the prognosis of the condition. Genetic testing (including cancer screening) is a small but extremely fast-growing component of the market, particularly in the services sector. Nearly all the MDx tests today are based on PCR (polymerase chain reaction) process, which is an enabling technology, generating faster, more specific and more sensitive detection of viral and bacterial infectious disease agents than culture and immunoassay type methods.

Currently, most of the DNA fragment analysis tools (genotyping) applied in laboratories utilize slab gel-based electrophoresis technologies, which have routinely been used for checking DNA properties since their inception more than 20 years ago. However, slab gel electrophoresis for DNA analysis (e.g., HLA SSP typing) is labor-intensive, low throughput and low resolution. Traditional gel-based electrophoresis methods currently used for DNA/RNA analysis take hours, if not days, to produce results with many cumbersome manual procedures, which are subject to human errors.

It is therefore desirable to develop a new system and method to improve resolving power, cost and throughput for genotyping.

SUMMARY OF THE INVENTION

The present invention provides a cost-effective multi-channel capillary gel-electrophoresis system for highly efficient, high throughput, nucleic acid-based analysis. This system can be used in laboratories to replace traditional slab gel electrophoresis devices for the high-speed and low cost applications of genetic testing (e.g., clinical applications of blood screening, infectious disease screening, and tissue typing and HLA/HIV/HPV/HCV genotyping). In one aspect of the present invention, a high-performance DNA analyzer system has been optimized for HLA SSP (Human Leukocyte Antigen Sequence Specific Primer) typing applications.

In one embodiment, the system uses a multiplexed fluorescence type detection mechanism, with an integrated fiber optic array-based technology and a novel disposable gel-cartridge. Twelve DNA samples are automatically injected, electrophoretically separated, detected and analyzed simultaneously by using a multiple usage and disposable multi-capillary gel-cartridge. For example, using commercially available DNA size markers as indicators, the system provides high resolving power with 12-channel separations in less than 1.5 minutes. The system can hold a total of 96 samples in a PCR plate that can automatically be analyzed within 25 minutes for a full plate of the HLA SSP kits.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF ILLUSTRATED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides a cost-effective multi-channel capillary gel-electrophoresis system for highly efficient, high throughput, nucleic acid-based analysis. This system can be used in laboratories to replace traditional slab gel electrophoresis devices for the high-speed and low cost applications of genetic testing (e.g., clinical applications of blood screening, infectious disease screening, and tissue typing and HLA/HIV/HPV/HCV genotyping). In one aspect of the present invention, a high-performance DNA analyzer system has been optimized for HLA SSP (Human Leukocyte Antigen Sequence Specific Primer) typing applications.

Capillary Electrophoresis

Capillary electrophoresis (CE) generally is a micro fluidic approach to electrophoresis (micro-channel device to simplify gel electrophoresis). Its greatest advantage is its diverse range of applications. CE technology is commonly accepted by the biotechnology industry specifically in the nucleic acid-based testing as a reliable, high resolution and highly sensitive detection tool. According to views of certain experts in the field, the nucleic acid-based testing will eventually become the method of choice and is expected to revolutionize healthcare by diagnosing previously elusive diseases, while also predicting patient outcomes and reducing cost.

CE with laser-induced fluorescence (LIF) is one of the most powerful analytical tools for rapid, high-sensitivity and high-resolution nucleic acid-based analysis/testing. However, due to the complexity of the equipment that detects and measures DNA samples and the difficulty in preparing the samples, the existing DNA analysis procedures are often time-consuming and expensive. However, CE-LIF-based multiple-channel systems with complicated scanning optical detection mechanisms are much more expensive than traditional slab gel-based DNA analysis systems. These expensive CE-LIF-based systems are thus out of reach for all but a few well-funded laboratories and seem to be a barrier for the expansion of the DNA analysis businesses.

It is therefore desirable to reduce the size, number of parts, and cost of equipment, to ease sample handling during the process, and in general, to have a simplified, low cost, high sensitivity detector, which would allow for simpler technologies/products that are sensitive, specific, high-throughput, cost-effective and rapid. Such tools will ultimately provide standardization for routine PCR-based DNA/RNA analysis.

BioCal Technology, Inc. (which is wholly owned by eGene, Inc.), the assignee of the present invention, developed a CE-based automated instrument (e.g., Model HDA-GT12 DNA Analyzer System). The illustrated embodiment of the automated instrument is based on BioCal's CE instrument, which incorporates low-cost and sensitive optical detection technology, integrated reagents cartridge and micro-fluidic electrophoresis principle for a real-time fluorescent analysis, to form a sensitive and accurate bioagent detection (genetic analysis) system. The system is designed to be high-throughput, easy-to-use, portable, inexpensive, very robust and for field operation/applications. The cartridge developed by BioCal (e.g., Model GC-HLA SSP specifically for HLA SSP typing) is designed to be supported by the instrument, with all essential cartridge elements aligned and coupled to support elements in the instrument. The cartridge is held with respect to sample trays that can be moved in relation to the capillary separation channels in the cartridge.

Overview of CE System

Figure 1:
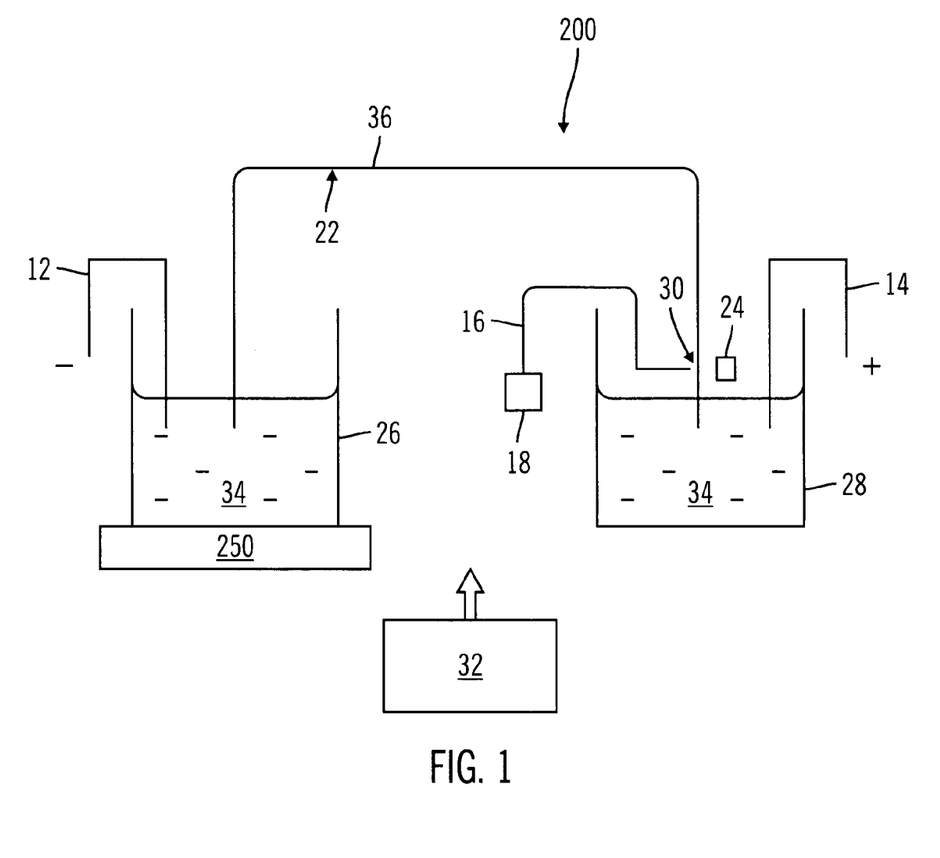
FIG. 1 is a schematic representation view of a capillary electrophoresis system in accordance with one embodiment of the present invention.

FIG. 1 is a schematic representation of a capillary electrophoresis (CE) system 200 in accordance with one embodiment of the present invention. The CE system 200 generally comprises a capillary separation column 22 (e.g., 200-500 μm O.D.), which defines a separation channel 36 (e.g., 25-200 μm I.D.). The capillary column 22 may be made of fused silica, glass, polyimide, or other plastic/ceramic/glassy materials. The inside walls of the separation column 22 (i.e., the walls of the separation channel 36) may be coated with a material that can build up an electrostatic charge to facilitate electrophoresis and/or electrokinetic migration of the sample components. The separation channel 36 is filled with a separation support medium, which may be a running buffer, or in the illustrated embodiment a sieving gel buffer specifically formulated for HLA SSP typing under the prescribed operating conditions). For radiation induced fluorescence detection, the gel matrix includes a known fluorophore, such as Ethidium Bromide.

One end of the capillary column 22 is submerged in a reservoir 28 of running buffer/gel 34. The other end of the capillary column 22 is coupled to the sample vial 26. It is understood that other detection configurations implemented in a system similar to the CE system 200. A radiation detector 24 is positioned outside a transparent section of the capillary walls at detection zone 30. An excitation fiber 16 extends from a radiation source 18 (e.g., LED or laser) and is directed at the detection zone 30 outside the walls of the column. Electrodes 12 and 14, that are part of the cartridge assembly are coupled to the buffer reservoirs 26 and gel reservoir 28 to complete the electrophoresis path.

Overview of CE Separation and Analysis

In operation, a prepared biological sample (e.g., a DNA/RNA sample) in the sample vial 26 is introduced into the far end of the capillary column 22 away from the detection zone 30 by any of a number of ways (e.g., electrokinetic injection from the sample reservoir). The sample binds to the fluorophore in the gel matrix supported in the capillary column 22.

When a DC potential (e.g., 1-30 KV) is applied between electrodes 12 and 14, the sample migrates under the applied electric potential along the separation channel 36 (e.g. DNA that is negatively charged travels through the sieving gel with an integrated dye matrix/fluorophore toward a positive electrode as shown in FIG. 1) and separates into bands of sample components (DNA fragments). The extent of separation and distance moved along the separation channel 36 depends on a number of factors, such as migration mobility of the sample components, the mass and size or length of the sample components, and the separation support medium. The driving forces in the separation channel 36 for the separation of samples could be electrophoretic, pressure, or electro-osmotic flow (EOF) means.

When the sample reaches the detection zone, excitation radiation is directed via the excitation fiber 16 at the detection zone. The sample components fluoresce with intensities proportional to the concentrations of the respective sample components (proportional to the amount of fluorescent tag material). The detector 24 detects the intensities of the emitted fluorescence at a wavelength different from that of the incident radiation. The detected emitted radiation may be analyzed by known methods. For the automated system, a controller 32 (discussed below in connection with FIG. 5) on the electronic board 64 (FIG. 4) controls the operations of the CE system 200.

Capillary Cartridge

In accordance with one aspect of the present invention, the capillary column for electropherisis may be a part of a removable cartridge that can be separated from the system for storage, transport or reuse. Different cartridges may be pre-assembled with different content, for example, a different gel-chemistry, with the content of the cartridge identified. Visual indicators may be provided to identify the cartridge and its contents. For example, a label (e.g., with a bar-code) or separate information sheet may be applied to the cartridge. In addition, in view of the reusability of the cartridge and defined usage or shelf life of the contents of the cartridge, a separate log may be associated with the particular cartridge for keeping track of the usage of the cartridge. A reusable capillary cartridge for use with a CE instrument could include a mechanism to automatically track information associated with a particular cartridge. The cartridge tracking data key feature is more fully described in copending patent application Ser. No. 11/022,313, which is fully incorporated by reference herein.

Figure 2:
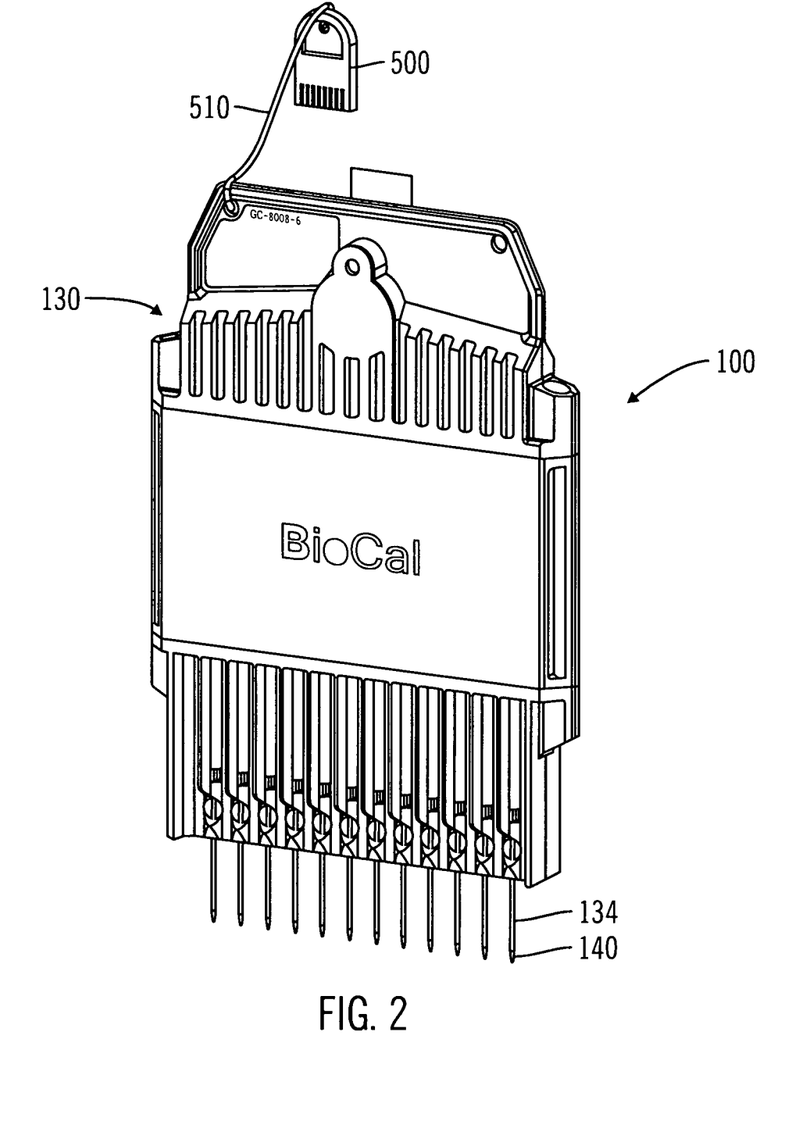
FIG. 2 is a perspective view of a capillary cartridge having a tracking device in accordance with one embodiment of the present invention.

FIG. 2 is a perspective view of the CE cartridge having a tracking data key in accordance with one embodiment of the present invention. The multi-channel capillary cartridge 200 includes twelve detection zones (schematically represented as 30 in FIG. 1), defined by capillaries 140 held in a cartridge body. A data key 500 is associated with the cartridge 100 (e.g., by a tether or cord 510 as shown). Details relating to the data key 500 is disclosed in copending application Ser. No. 11/022,313. The cartridge 100 includes a twelve-channel fused silica capillary array that is used for separation and detection of the samples as part of a disposable and/or portable, interchangeable cartridge assembly 100. The cartridge 100 shown in FIG. 2 holds up to 12 capillaries 140, 12-18 cm long. The cartridge 100 is integrated with a top, outlet buffer reservoir 130 common to all capillaries 140, which, when the cartridge 100 is installed in the CE system shown in FIGS. 3 and 4 (discussed below) is directly coupled by the interface mechanism 300 to a modular compressed gas source 78, such as a replaceable pressurized gas cartridge of an inert, compatible or non-reactive gas (e.g., Nitrogen, compressed air, $CO_2$, etc.) or a pressure pump. Appropriate pressure plumbing, including tubing, pressure valve and solenoid controls, is provided. (Details of such plumbing are omitted, since it is well within one skilled in the art to configure such plumbing given the disclosure herein of the functions, features and operations of the system 200.) The pressure source 78 provides the required gas pressure to fill-up all the 12-capillaries with the sieving gel contained in the reservoir 130 and to purge the gel from the previous run from the capillaries during the refilling process. Depending on the viscosity of the gel, pressures of up to 40 PSI may be applied to the capillaries 140 through the gel-filled reservoir 130.

Figure 6:
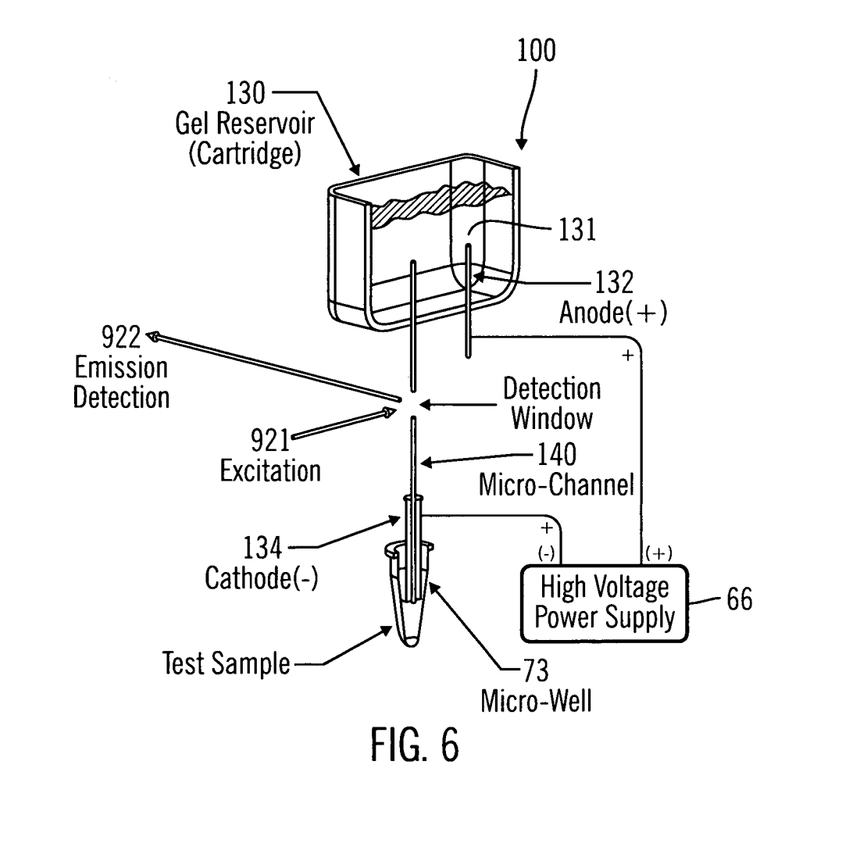
FIG. 6 is a schematic view of the capillary cartridge in relation to detection system and applied power in accordance with one embodiment of the present invention.

Referring to FIG. 6, the gel-cartridge 100 includes an integrated reservoir 130 containing a separation support medium (e.g., a gel matrix buffer) 131, which is common to all capillaries 140. The chemistry of the medium 131 and the characteristics of the capillaries 140 (e.g., capillary size, coating and length) are defined for each cartridge 100. The disposable gel-cartridges 100 can be packaged with small bore I.D. capillaries (i.e. 10-50 µm ID, 12-20 cm long) combined with low current (i.e., at low resistivity) and low viscosity type formulated linear polymer gel-matrix to provide high speed (shorter separation time) and higher resolution separations of DNA fragments. The smaller bore capillaries (12-capillary cartridge) combined with the special formulated separation buffer/gel-matrix can achieve 250 or more continuous runs with a total current of <120 µA without any damage to the gel matrix or loss of overall separation resolution.

The cartridge gel-reservoir 130 is equipped with a built in common electrode anode 132 (equivalent to anode 14 in FIG. 1) for all 12-capillaries 140, and each depending end of the capillaries 140 is provided with an external coaxial cathode 134. The anode 132 and cathodes 134 are automatically connected by the interface mechanism 300 to the high voltage power supply 76 (FIG. 4) for electrophoresis when installed inside the system 200. A fan or Peltier cooler (not shown) on the adjacent structure to the cartridge 100 may be provided to provide temperature control of the cartridge. In addition or in the alternate, the cartridge may have vent holes (input and output) for air circulation (temperature controlled air to be introduced to the cartridge from the instrument side). Depending on the heat generated during CE separation, the cartridge may simply be exposed to ambient temperature, with no auxiliary cooling features.

Figure 3:
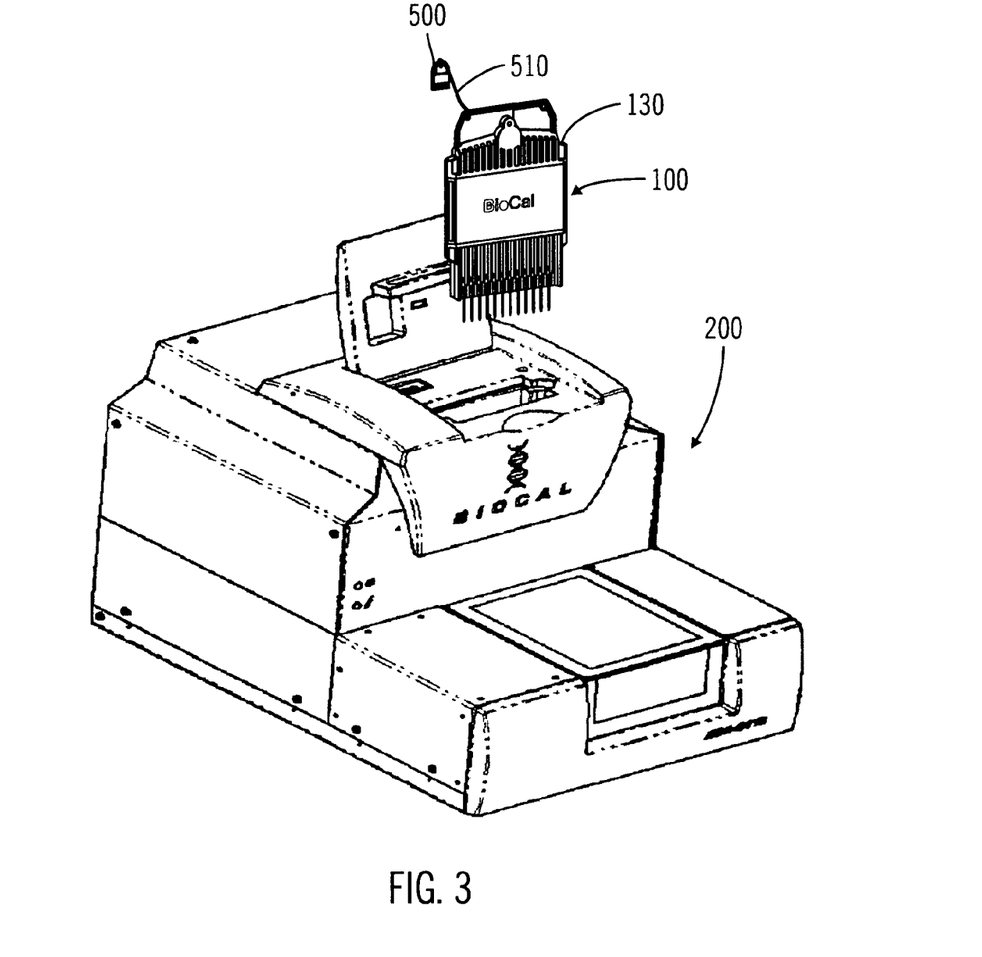
FIG. 3 is a perspective external view of a bio-analysis instrument that uses the capillary cartridge of FIG. 2, in accordance with one embodiment of the present invention.
Figure 4:
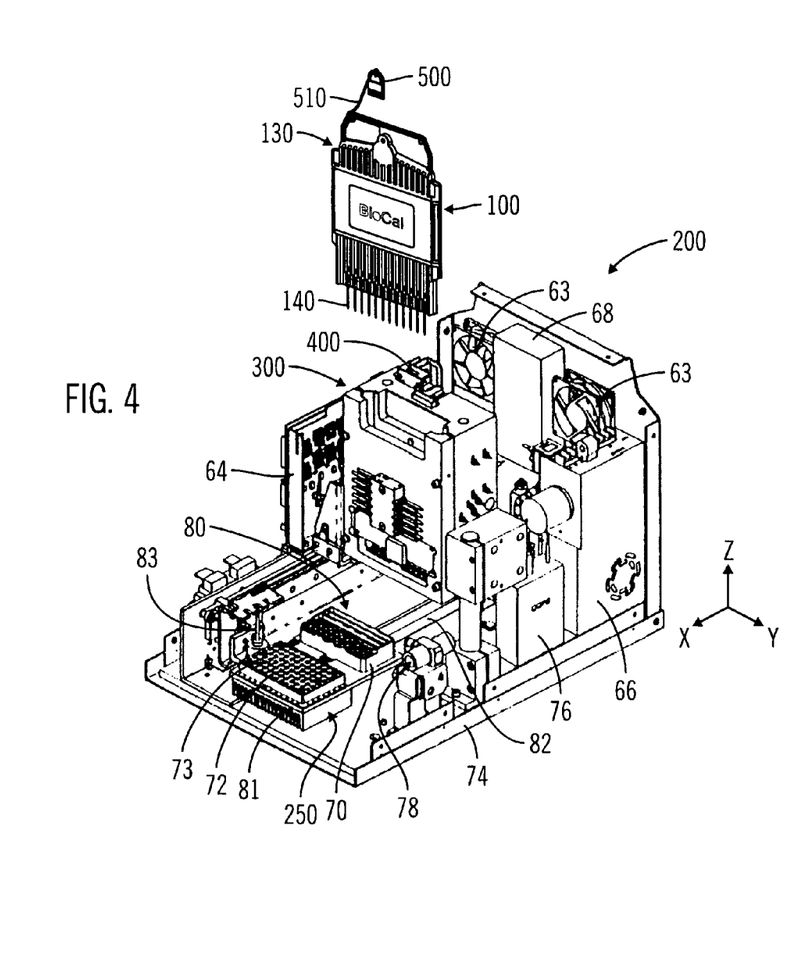
FIG. 4 is a perspective internal view of the bio-analysis instrument of FIG. 3, in accordance with one embodiment of the present invention.

In one embodiment, the cartridge 100 is received in the automated CE system 200 shown in FIGS. 3 and 4. A power supply 66 (FIG. 4) provides DC power to the CE system 200 to be supplied to the cartridge, as will be further explained below.

Further details of the cartridge may be referenced to the copending application Ser. No. 10/059,993, which is fully incorporated by reference herein.

Multiple Capillary Cartridge Based CE System

FIG. 4 shows an overall perspective view of the internal components of the CE system 200 (e.g., a DNA Analyzer). FIG. 3 is an external view of the system. The CE system 200 incorporates an interface mechanism 300, in accordance with one embodiment of the present invention. The interface mechanism 300 supports a multi-channel cartridge 100 in accordance with the one embodiment of the present invention, which provides easy handling of multi-channel separation columns, and allows easy optical coupling of the detection zones to the detection optics of the CE system 200.

The fully automated DNA analysis system 200 has a base 74, supporting a modular X-Z mechanism 80 having a sample tray support frame 81. The X-Z mechanism 80 supports and moves a buffer plate 70 in relation to the multi-capillary cartridge 100 supported by the interface mechanism 300, and a sample holder (e.g., a 96-well micro-titer plate 72) which may be held in an optional PCR sample preparation device 250. Specifically, the mechanism 80 comprises an X mechanism 82 for moving the support frame 81 along the X-direction relative to the cartridge 100, and a Z mechanism 83 for moving the cartridge in the Z direction relative to the support frame 81. The PCR sample preparation device 250, if provided, may be controlled by a PCR thermoelectric controller 68 (see FIG. 5). Additional details concerning the PCR sample preparation device 250 may be referenced to U.S. patent application Ser. No. 10/973,828, which has been fully incorporated by reference herein.

Figure 7:
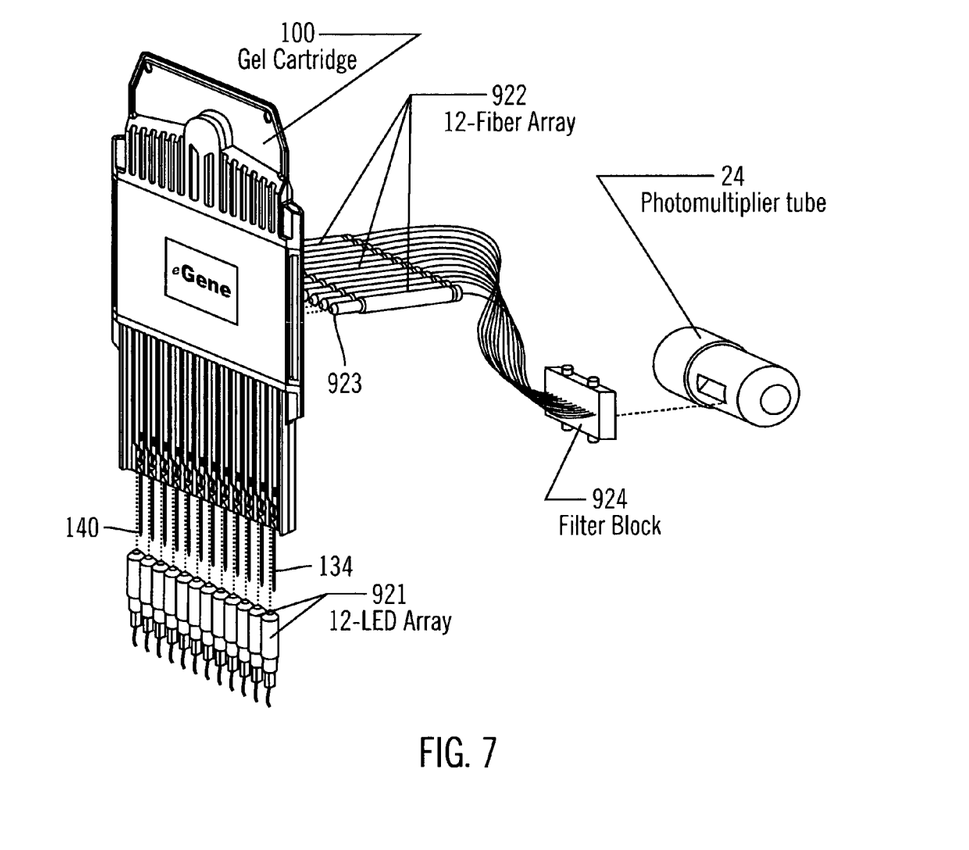
FIG. 7 is a partial perspective view of the capillary cartridge in relation to detection system in accordance with one embodiment of the present invention.

Referring also to FIGS. 6 and 7, twelve excitation LEDs 921 are time-multiplexed (with a sampling frequency of 10-100 Hz), producing multiplexed signals to the 12 separation micro-channels (capillary tubes 140) and proportionally twelve time-staggered emitted fluorescence signals (FIG. 7) are then collected by 12-micro-ball lenses 923 and are coupled to twelve emission detection optical fibers (12-fiber array) 922, which are relayed down to a single photomultiplier tube (PMT detector) 24 via a filter block 924. The gel-cartridge 100 supports 12 fused silica capillaries 140 for CE separation (FIGS. 6 and 7).

Other structures and operations of the interface mechanism 300 of the CE system 200 may be referenced to the copending U.S. patent application Ser. No. 10/823,382, which is fully incorporated by reference herein. The cartridge interface accomplishes quick and reliable interface connections to the disposable gel contained capillary cartridge 100. These interface connections include a gas pressurization connection (not shown in FIG. 7), high voltage connections (anode 132 and cathodes 134), and precision optical connections. The interface also provides precise and repeatable mechanical positioning of the cartridge, to accurately position the components of the cartridge in relation to the support elements in the CE system 200, including positioning the capillary tips in relation to external sample or buffer reservoirs, found on 96-well titer plate, for example. Additionally, given the interface provides separate electrical, optical and pneumatic connections to each separation channel, there would be channel-to-channel isolation from cross talk both electrically and optically and insulation to the rest of the instrument from high voltage.

Detection System

U.S. Pat. No. 6,828,567 is fully incorporated by reference herein, which more specifically discloses the time staggered/multiplexed detection scheme that can be adopted in the CE system 200.

Control of the Automated System 200

The CE system 200 provides an integrated controller to operate the various components of the system. The operations of the CE system 200, including the interface mechanism 300 with the I/O port 400, detection system, power supply, X-Y control system, etc., are controlled by a controller 32 interfacing with an external user control interface (e.g., a PC 918), to coordinate the functions described herein.

Figure 5:
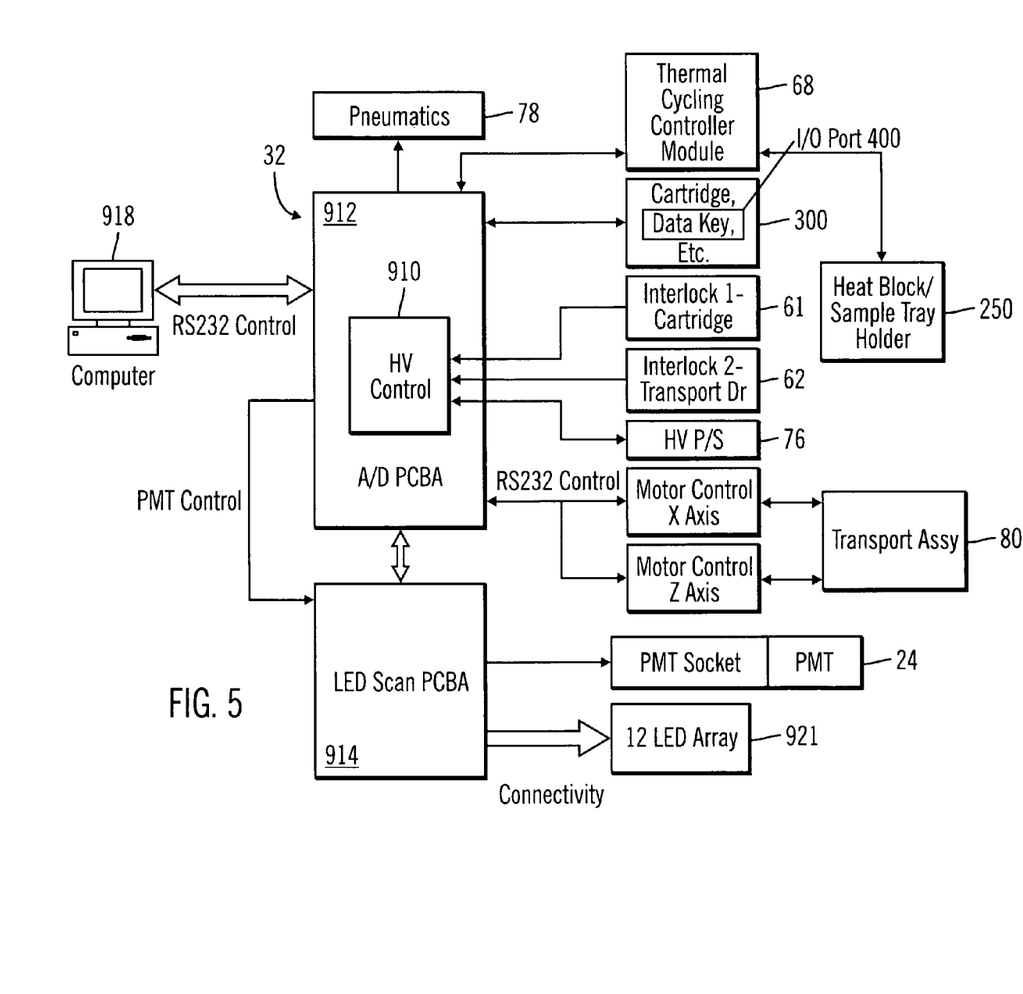
FIG. 5 is a block diagram of the control system for the bio-analysis instrument in accordance with one embodiment of the present invention.

Referring also to FIG. 5, in accordance with one embodiment of the present invention, the block diagram of the controller 32 for the CE system 200 is illustrated. The controller 32 comprises a processor as part of the A/D Board (LED Processor PCBA) 912 with CPU 910 for converting detection signals received from the detector 24 (e.g., a PMT) to corresponding digital signals, coming from LEDScan PCBA interface 914 for transferring and receiving signals to and from respective parts of the CE system 200 by instructions from the CPU 910. The A/D (LED Processor PCBA) interface 912 is coupled to the various actuators and the I/O port 400 in the interface mechanism 300 to control and connect (using the interface mechanism 300) at least high voltage power supply 76, pneumatics 78 (hidden from view in the interface mechanism 300 in FIG. 2), motor controls (X-Z sample/buffer tray) 80 and interlocks (cartridge and transport doors) 61 and 62 (details of these are not shown in the interface mechanism 300 in FIG. 2). The A/D or LED Processor PCBA 912 also controls the high-voltage power supply 76 for sample injection and electrophoresis functions of the CE system 200, a circuit 914 (LEDScan Board) for modulating the excitation radiation source (e.g., LEDs) 921 and the detector module 24 of the CE system 200. Details of the modulation of the excitation radiation source may be referenced to copending U.S. patent application Ser. No. 10/060,052, which had been fully incorporated by reference herein.

The A/D (LED Processor PCBA) 912 may be further coupled to an external personal computer 918, which in turn performs data processing or additional control function for the CE system 200, e.g., using BioCal's BioCalculator Software to control various features and functions of the automated multi-channel CE system 200 (including the optional integrated PCR sample preparation device).

The components of the controller 32, with the exception of the PC 918, may be packaged as an electronic board 64 (FIG. 4) and cooling fans 63, on board the CE system 200 and electrically coupled to the PC 918 via a serial port (not shown), or they may be part of a separate controller module outside of the CE system 200. The CPU 910 and/or the PC 918 are programmed to accomplish the various control functions and features for the CE system 200. In one embodiment, the PC 918 can be configured to provide the user control interface for the CE system 200 (e.g., user initiation of the connection sequence of the interface mechanism 300). It would be within a person skilled in the art to implement the program code given the functions and features disclosed herein. In an alternate embodiment, the controller 32 or components thereof may be incorporated as part of the PC 918.

Operation of CE System

Once the capillary cartridge 100 and the data key 500 have been mated to the instrument, the cartridge ID and the number of pre-programmed runs available from the cartridge 100 are read by the CE system 200 via the I/O port 400. The CE system 200 may employ an algorithm to determine if the capillary cartridge 100 has enough runs left to complete the process cycle before initiating the CE sequence. Otherwise, the CE system 200 may display an error message and the sequence is stopped. If it is determined that the capillary cartridge 100 has sufficient runs available, the CE sequence will start and number of runs is tracked by the CE system. At the end of the analysis, the number of remaining runs is calculated and sent to the data key 500 for storage.

The controller 32 of the instrument may be configured to "authenticate" the cartridge 100 and conduct an integrity check to determine if the particular cartridge 100 has the correct properties (e.g., gel-chemistry, number of channels/capillaries) for the particular sample analysis to be conducted. The instrument may also confirm that the user falls within the class of users permitted to use the particular cartridge. Further, the instrument may communicate/record information concerning usage of the cartridge 100 (e.g., usage history, sequence/method steps/parameter settings, patient I.D., test parameters, and perhaps test results). Such information provides an update to the stored information from the previous use of the cartridge. Further reading and writing can be controlled with respect to the data and information discussed above relating to the data key 500. The instrument may go through other checks to authenticate the test protocols the user wants to apply to the particular cartridge is proper, to determine if there are any limitations, restrictions or constraints, such as those noted before.

In operation of the CE analysis, the sample handling tray transport mechanism 80, with a 96-well plate (8×12) 72 and buffer tray 70, is used to introduce the amplified DNA samples (or analytes) to each capillary 140. The X-Z transport mechanism 80 indexes a row of sample carrying wells 73 in the micro-titer plate 72 under the row of capillary tips 140 and dip the tips into the well. By applying a voltage, electrokinetic injection moves a known amount of the DNA sample to the beginning of the separation column 140. After injection, the DNA samples from sample tray 72 may be replaced with a running buffer from tray 70. Alternatively, after injection, the transport mechanism 80 may index to move a row of 12 wells of the titer plate 72 into position under the capillaries 140 of the cartridge 100 to replace the twelve wells containing DNA samples.

By applying high voltage across the total length of the capillary 140, separation of the DNA sample into DNA fragments is achieved. As the fragments approach the end of the capillaries 140 and enter into the detection zone, the excitation light energy (e.g., from twelve LEDs delivered by optical fibers) is directed at the detection zone, illuminating the migrating DNA fragments. The detection scheme may be in a time-staggered manner as disclosed in U.S. Pat. No. 6,828,567, which has been incorporated by reference herein.

To prepare for the next run with a different sample, the old gel from the previous run is purged from the capillaries by pressuring the reservoir to refill the capillaries with fresh gel. The trays 70 carry cleaning solutions, waste collection, and samples. The purged gel is collected by one of the trays 70 by positioning the tips of the capillaries at a row of waste collecting wells in one of the trays. The tips of the capillaries may be cleaned with water or a cleaning solution by positioning and dipping the tips of the capillaries in such solution in the appropriate tray wells. When the capillaries are refilled and ready for the next run, the tips of the capillary are dipped into the samples by repositioning the tray 72. The above mentioned sequence of process may be programmed as one of the automated functions of the controller 32. The interface mechanism 300 provides the interfacing of support elements in the CE system 200 to the cartridge, such as high voltage, gas pressure, LED radiation source, and detection optics, as described above.

After the analysis has been completed, the cartridge 100 may be retrieved and reused when needed for another analysis at a later time or date. If a different run condition is contemplated, a different cartridge having different attributes and properties may be used instead. The data key mechanism of the present invention would automatically keep track of the usage of the different interchangeable cartridges, without requiring the user to manually keep track of such.

Genotyping Application

The afore-described genetic analysis system is optimized for high speed HLA SSP typing. The HDA-GT12™ Genetic Analysis System for the HLA SSP typing provides a large-volume and low-cost molecular diagnostics and genotyping detection platform alternative to the slab gel type tools, that can also be used for other type applications such as HIV, HBV, HCV, HPV and pharmacogenomics.

The capillary cartridges with smaller ID capillaries (10-50 μm I.D.) are able to run with much higher voltages of up to 15-20 KV for a very fast type separation (<2 minute), which is able to resolve 20 bp (base pair) useful for fast DNA sizing (HLA SSP type genotyping) applications and for high-throughput molecular diagnostic (MDx) type applications. Automated and high speed separation, detection tools and devices are essential for the large volume genotyping labs, such as the HLA & molecular tissue typing core labs to provide faster turn around time and lower cost solutions for the rapid organ matching type needs. The HLA labs are extremely cost conscious and in order for a new technology/tool to replace the existing labor intensive slab gel electrophoresis tools and methods of the manual gel preparation, high voltage electrophoresis process and time consuming gel documentation process a fully automated single push button process is needed (a must) to completely reduce human errors, lower cost per sample and totally digitize the data interpretation process.

In accordance with one embodiment of the present invention, a linear polymer solution is used for the gel sieving matrix. The linear polymer solution comprises between about 0.01% and about 1.5% polyethylene oxide ("PEO"); between about 0.0% and less than about 2.0% of a second polyethylene glycol ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

In a preferred embodiment the matrix has the following components:

|  | mwt g/mol | Concentration |
|---|---|---|
| PEO | 7000000 | 0.000607 mM |
| PEO | 900000 | 0.002777778 mM |

-continued

|  | mwt g/mol | Concentration |
|---|---|---|
| MOPS |  | 12.5 mM |
| Tris |  | 7.85 mM |
| NP40 |  | 0.05% |
| NaN3 |  | 1 mM |
| EtBr |  | 10 mM |

A DNA intercalating dye (Ethidium Bromide (EtBr) is provided within the sieving gel, so that as the DNA fragments move through the sieving gel, the dye allows the migrating DNA fragments to be detected. Experiments have shown that detection sensitivities of 100 ng/ml (0.02 ng of the Hae III digest φX174 DNA test mix) (e.g., FIGS. 8 and 10) are achievable, which is several orders of magnitude better than conventional slab gel electrophoresis devices using the same intercalating dye.

A total DNA volume of 5-10 μl (PCR product) in a 12 well strip or 96-well PCR plate format can directly be introduced to the genotyping system described above, which then by a simple push of a button the automated process starts. The samples are (typically 5 μg/ml in DNA concentrations) injected electrokinetically into the 12-capillary gel columns of the cartridge by the applied voltages of up to 15 KV at 5-20 seconds. The electrophoresis is carried out under 15 KV at 120 μA current for a total of 1.5 minutes run time per row of the 96-well plate, and it completes the full plate separation and analysis in 25 minutes which includes the cycle time as well.

Figure 8:
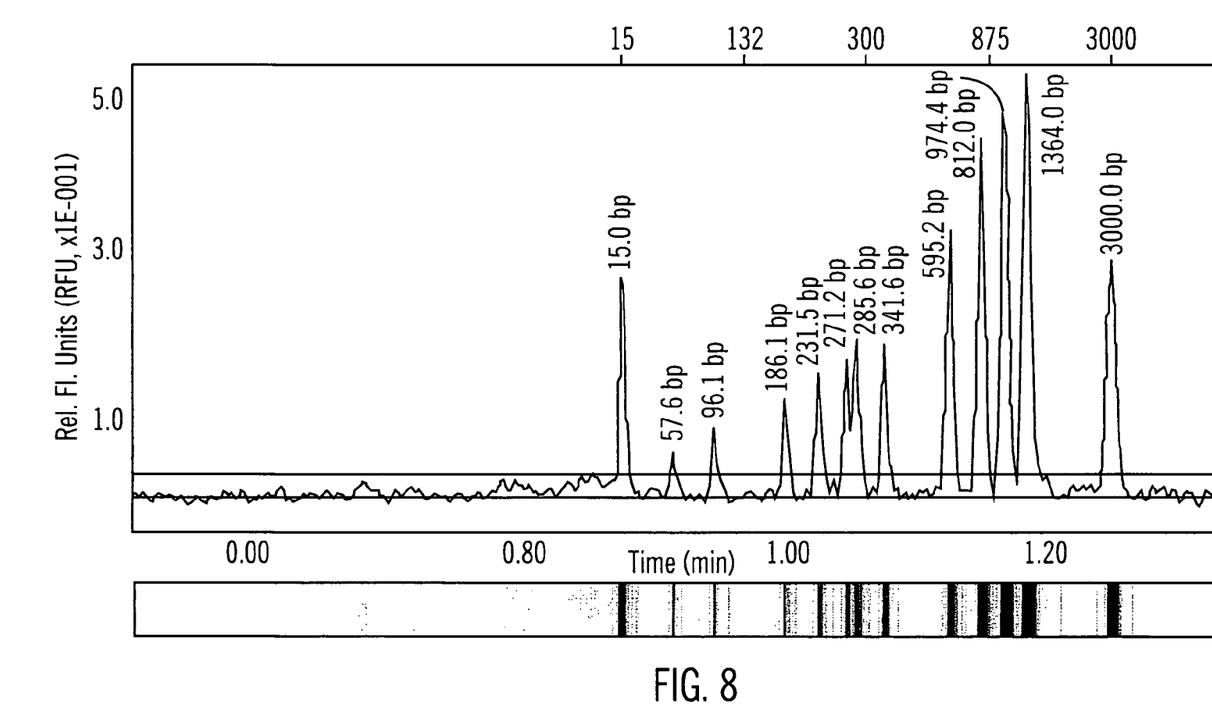
FIG. 8 is an electropherogram representing the high speed and high-resolution results of the DNA Size Marker electrophoresis using the capillary cartridge in accordance with one embodiment of the present invention.

FIG. 8 shows the electropherogram and corresponding gel view representing the high speed and high-resolution results of the DNA Size Marker (phiX174 Hae III dsDNA fragments) electrophoresis using the 12-capillary gel-cartridge. The electropherogram shows 72 bp to 1,353 bp separations in less than 1.5 minutes (GC-HLA SSP gel cartridge) for all the 12 channels still maintaining high separation resolution of 10 bp at 271 and 281 bp.

Figure 9:
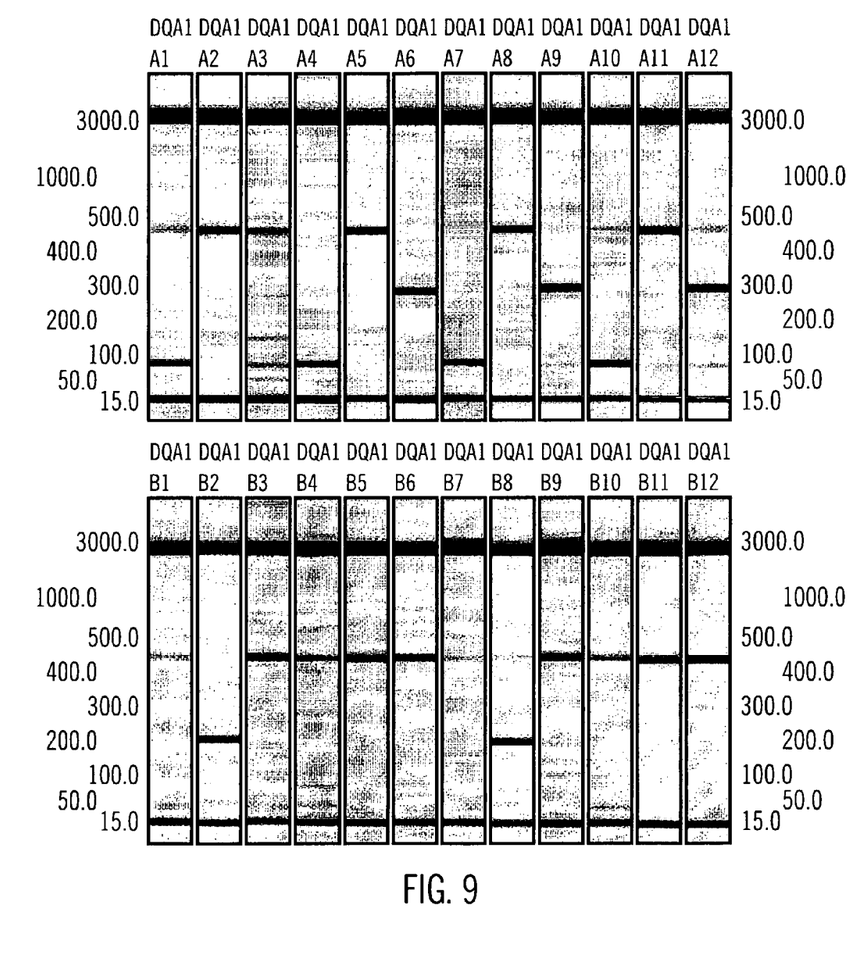
FIG. 9 is a gel-image of 24 HLA samples analyzed by the HDA genotyper (GenoVision HLA SSP DQA1 samples).

FIG. 9 shows the gel-image of 24 HLA samples analyzed by the HDA genotyper (GenoVision HLA SSP DQA1 samples). The gel-image has been transformed from the detected optical detection data for each capillary channel, into an image representing tracks of separation bands which similar to separation image typically represented for gel slab separation which is familiar to a laboratory user.

Figure 10:
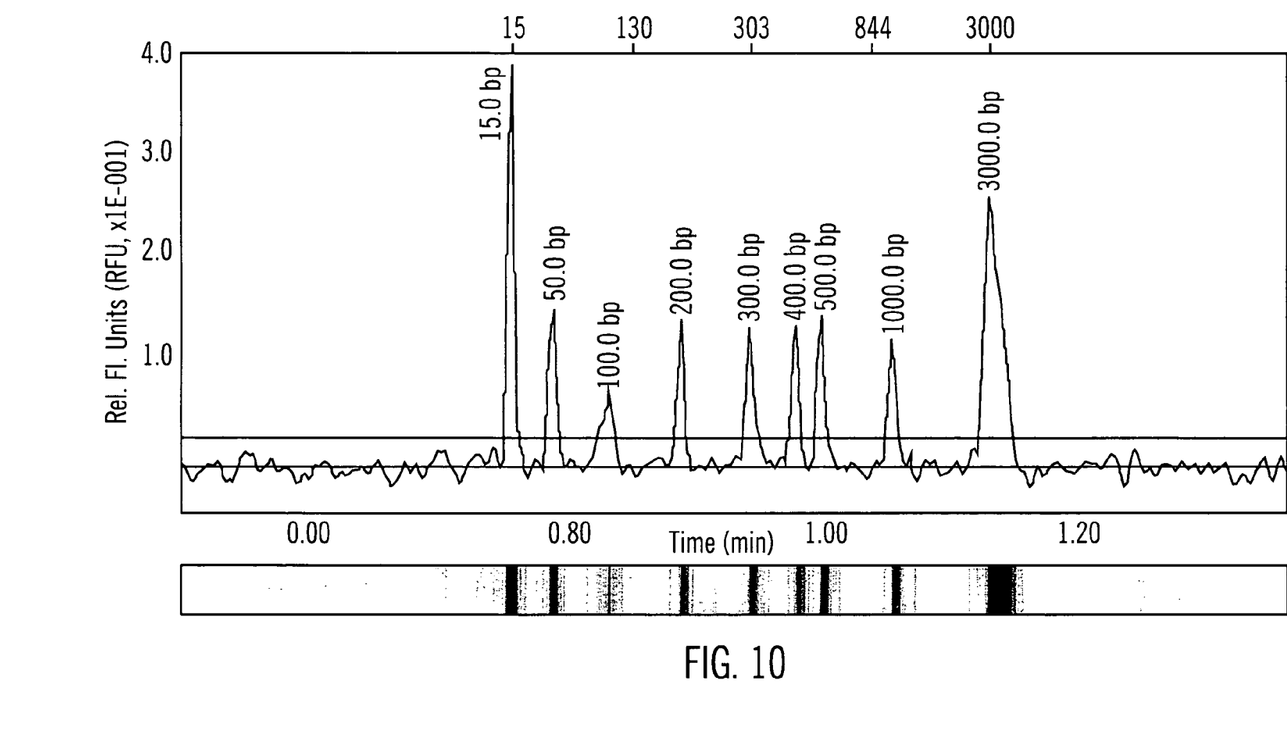
FIG. 10 is an electropherogram and corresponding gel view of the DNA Size Marker in between the two Alignment Markers (the 15 bp Lower Marker and the 3000 bp Upper Marker).

FIG. 10 shows the another example of an electropherogram and corresponding gel view of the DNA Size Marker in between the two Alignment Markers (the 15 bp Lower Marker and the 3000 bp Upper Marker).

Simplifying the optical detection system design of the HDA-GT12™ system for the HLA SSP typing was done by utilizing fiber optics and micro-optics fluorescence detection technologies. The design reduces the overall manufacturing cost, while improving the reliability of the instrument. Even though the chemistry cost per test is less than half that of slab gel systems, the system produces high resolution and detection sensitivity only found in the high-end capillary gel electrophoresis systems (the larger and costly sequencing type instruments). The HLA SSP gel cartridges are designed to produce high speed electrophoretic results using a programmed automated method outlined in FIG. 11. Specifically, FIG. 11 shows a "DM80 Method" programmed in the HDA-GT12™ system for the HLA runs, showing: an initial purge of the capillaries for 5.0 seconds in the wash position, an injection of the Alignment Marker at 15.0 KV for 8.0 seconds, a DNA sample injection at 15 KV for 8.0 seconds, electrophoresis separation at 15.0 KV for 80 seconds with the capillary tips in the buffer position.

Figure 11:
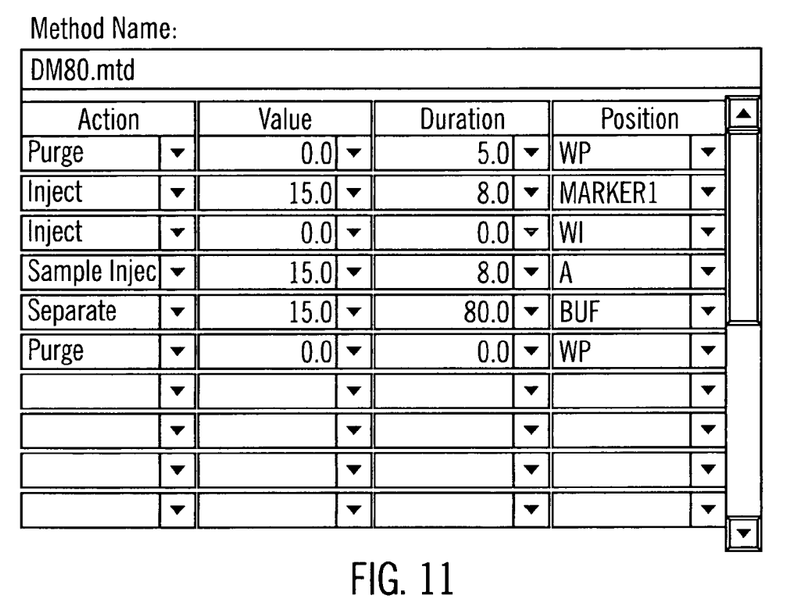
FIG. 11 is a table showing DM80 Method used for the HLA runs showing the Alignment Marker and DNA sample injections at 15 KV for 8 seconds and the 80 seconds separations in the buffer position.

The BioCalculator-HLA software provides a full automated cartridge prep, gel purging, marker injection, DNA sample injection and buffer separation sequence and final analyses results within 80 seconds per row for a 12 channel type cartridge using the automated method according to the programmed sequence of steps and operation parameters shown in FIG. 11.

It has been demonstrated that the gel cartridge with an integrated gel-reservoir under the above mentioned running conditions is able to achieve multiple runs (more than 400 runs) with reproducible results (substantially the same separation efficiency, power and resolution) with no need for gel replacement and column cooling devices. Cartridge life tests have shown that after continuous high voltage runs the gel matrix does not degrade since it is drawing low operating currents with constant applied DC voltages. Shorter separation times (<2 minutes) prevents high voltage shock, reduced operating temperatures and longer gel-cartridge life. The gel-cartridge system/device is used for multiple electrophoresis runs (250 or more) in an automated electrophoresis device of the HDA-GT12 without gel replacement, which provides advantages for non stop, high-throughput, fast sample screening and very low-cost per sample applications of HLA SSP typing.

While the invention has been particularly shown and described with reference to the preferred embodiments, it will be understood by those skilled in the art that various changes in form and detail may be made without departing from the spirit, scope, and teaching of the invention.

For example, interface mechanisms may be adapted to receive capillary cartridges of other structural designs. By way of example and not limitation, the detection scheme of the present invention is described in connection with capillary electrophoresis and radiation induced fluorescence detection. It is understood that the present invention is also applicable to detection of radiation emissions other than fluorescence emissions, including other types of emissive radiation, such as phosphorescence, luminescence and chemiluminescence, as well as UV and Visible absorbance based detection. Furthermore, while the separation channels in the described embodiments are defined by cylindrical columns or tubes, it is understood that the concepts of the present invention is equally applicable to separation channels defined by channels, for example micro-channels (such as square, rectangular or essentially semicircular cross sections) defined by etching or micro-machining in a substrate (micro-fluidics type devices or bio-chips).

Accordingly, the disclosed invention is to be considered merely as illustrative and limited in scope only as specified in the appended claims.

We claim:

1. A cartridge for bio-analysis, comprising:
a body;
a plurality of capillaries supported by the body;
a reservoir common to the capillaries; and
a linear gel matrix formulated for genotyping contained in the reservoir, wherein the gel matrix comprises a linear polymer solution as a gel sieving matrix, wherein the linear polymer solution comprises:

|  | mwt g/mol | Concentration |
|---|---|---|
| PEO | 7000000 | 0.000607 mM |
| PEO | 900000 | 0.002777778 mM |
| MOPS |  | 12.5 mM |
| Tris |  | 7.85 mM |
| NP40 |  | 0.05% |
| NaN3 |  | 1 mM |
| EtBr |  | 10 mM. |

2. A bio-analysis system, comprising:
a base;
a cartridge as in claim 1;
a cartridge interface support on the base, interfacing with the cartridge system; and
a controller operatively coupled to the cartridge interface to control operations of the cartridge interface.

3. A method of genotyping, comprising:
providing a cartridge, which comprises:
a body;
a plurality of capillaries supported by the body;
a reservoir common to the capillaries; and
a linear gel matrix formulated for genotyping contained in the reservoir;
introducing a sample into one end of each capillary;
undertaking electropherisis separation along each capillary, to separate the sample into components to be analyzed,
wherein the gel matrix comprises a linear polymer solution as a gel sieving matrix, wherein the linear polymer solution comprises:

|  | mwt g/mol | Concentration |
|---|---|---|
| PEO | 7000000 | 0.000607 mM |
| PEO | 900000 | 0.002777778 mM |
| MOPS |  | 12.5 mM |
| Tris |  | 7.85 mM |
| NP40 |  | 0.05% |
| NaN3 |  | 1 mM |
| EtBr |  | 10 mM. |

4. The cartridge of claim 1, wherein the gel matrix is formulated for HLA SSP (Human Leukocyte Antigen Sequence Specific Primer) typing.

5. The cartridge of claim 4, wherein the gel matrix comprises a linear polymer solution as a gel sieving matrix, wherein the linear polymer solution comprises between about 0.01% and about 1.5% polyethylene oxide ("PEO"); between about 0.0% and less than about 2.0% of a second polyethylene oxide ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

6. The cartridge of claim 1, wherein the gel matrix comprises a linear polymer solution as a gel sieving matrix, wherein the linear polymer solution comprises between about 0.01% and about 1.5% polyethylene oxide ("PEO"); between about 0.0% and less than about 2.0% of a second polyethylene oxide ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

7. The method as in claim 3, wherein the gel matrix is formulated for HLA SSP (Human Leukocyte Antigen Sequence Specific Primer) typing.

8. The cartridge of claim 7, wherein the gel matrix comprises a linear polymer solution as a gel sieving matrix, wherein the linear polymer solution comprises between about 0.01% and about 1.5% polyethylene oxide ("PEO"); between about 0.0% and less than about 2.0% of a second polyethylene oxide ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

9. The cartridge of claim 3, wherein the gel matrix comprises a linear polymer solution as a gel sieving matrix, wherein the linear polymer solution comprises between about 0.01% and about 1.5% polyethylene oxide ("PEO"); between about 0.0% and less than about 2.0% of a second polyethylene oxide ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

10. A cartridge for bio-analysis, comprising:
a body;
a plurality of capillaries supported by the body;
a reservoir common to the capillaries; and
a gel matrix formulated for genotyping contained in the reservoir, wherein the gel matrix comprises a polymer solution as a gel sieving matrix, wherein the polymer solution comprises first and second polyethylene oxide (PEO) polymers having substantially different molecular weights, each in a very small concentration, wherein the first and second PEO polymers are about 7.8 times different in molecular weights.

11. The cartridge of claim 10, wherein the first and second PEO polymers have different concentrations.

12. The cartridge of claim 11, wherein the concentrations of the first and second PEO polymers are substantially different.

13. The cartridge of claim 10, wherein the concentration of the first PEO polymer is about 0.000607 mM.

14. The cartridge of claim 13, wherein the concentration of the second PEO polymer is about 0.002777778 mM.

15. The cartridge of claim 10, wherein the concentration of the second PEO polymer is about 0.002777778 mM.

16. The cartridge of claim 10, wherein the molecular weight of the first PEO polymer is about 7000000 mwt g/mol.

17. The cartridge of claim 16, wherein the molecular weight of the second PEO polymer is about 900000 mwt g/mol.

18. The cartridge of claim 10, wherein the molecular weight of the second PEO polymer is about 900000 mwt g/mol.

19. The cartridge of claim 10, wherein the molecular weight of the first PEO polymer is larger than the molecular weight of the second PEO polymer, and the concentration of the first PEO polymer is smaller than the concentration of the second PEO polymer.

20. The cartridge of claim 19, wherein the concentrations of the first and second PEO polymers are substantially different.

21. The cartridge of claim 20, wherein the first PEO polymer has a molecular weight of substantially 7000000 mwt g/mol and a concentration of substantially 0.000607 mM, and the second PEO polymer has a molecular weight of substantially 900000 mwt g/mol and a concentration of substantially 0.002777778 mM.

22. The cartridge of claim 10, wherein the first and second PEO polymers are linear polymers.

23. The cartridge of claim 10, wherein the gel matrix comprises a linear polymer solution as a gel sieving matrix, wherein the linear polymer solution comprises between about 0.01% and about 1.5% polyethylene oxide ("PEO"); between about 0.0% and less than about 2.0% of a second polyethylene oxide ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

24. A method of genotyping, comprising:
providing a cartridge, which comprises:
a body;
a plurality of capillaries supported by the body;
a reservoir common to the capillaries; and
a gel matrix formulated for genotyping contained in the reservoir;
introducing a sample into one end of each capillary;
undertaking electrophoresis separation along each capillary, to separate the sample into components to be analyzed,
wherein the gel matrix comprises a polymer solution as a gel sieving matrix, wherein the polymer solution comprises first and second PEO polymers having substantially different molecular weights, each in a very small concentration, wherein the first and second PEO polymers are about 7.8 times different in molecular weights.

* * * * *